(12) United States Patent
Lindsay et al.

(10) Patent No.: US 10,145,846 B2
(45) Date of Patent: Dec. 4, 2018

(54) DIGITAL PROTEIN SENSING CHIP AND METHODS FOR DETECTION OF LOW CONCENTRATIONS OF MOLECULES

(71) Applicant: Arizona Board of Regents on behalf of Arizona State University, Scottsdale, AZ (US)

(72) Inventors: Stuart Lindsay, Phoenix, AZ (US); Peiming Zhang, Gilbert, AZ (US); Pei Pang, Tempe, AZ (US)

(73) Assignee: ARIZONA BOARD OF REGENTS ON BEHALF OF ARIZONA STATE UNIVERSITY, Scottsdale, AR (US)

( * ) Notice: Subject to any disclaimer, the term of this patent is extended or adjusted under 35 U.S.C. 154(b) by 41 days.

(21) Appl. No.: 15/303,960

(22) PCT Filed: Apr. 16, 2015

(86) PCT No.: PCT/US2015/026241
§ 371 (c)(1),
(2) Date: Oct. 13, 2016

(87) PCT Pub. No.: WO2015/161119
PCT Pub. Date: Oct. 22, 2015

(65) Prior Publication Data
US 2017/0038369 A1 Feb. 9, 2017

Related U.S. Application Data

(60) Provisional application No. 61/980,317, filed on Apr. 16, 2014.

(51) Int. Cl.
*G01N 33/543* (2006.01)
*B01L 3/00* (2006.01)
*G01N 33/487* (2006.01)

(52) U.S. Cl.
CPC .... *G01N 33/5438* (2013.01); *B01L 3/502715* (2013.01); *B01L 3/502761* (2013.01);
(Continued)

(58) Field of Classification Search
CPC .......... G01N 33/5438; G01N 33/48721; B01L 3/502761; B01L 3/502715
See application file for complete search history.

(56) References Cited

U.S. PATENT DOCUMENTS 6,824,974 B2 11/2004 Pisharody et al.
8,628,649 B2 1/2014 Lindsay et al.
(Continued)

FOREIGN PATENT DOCUMENTS

WO WO 2013/116509 A1 8/2013

OTHER PUBLICATIONS

Archakov, A.I. et al., "AFM Fishing Nanotechnology is the Way to Reverse the Avogadro Number in Proteomics" Proteomics 2007, 7, pp. 4-9.
(Continued)

*Primary Examiner* — Melanie Yu Brown
(74) *Attorney, Agent, or Firm* — Schwabe, Williamson & Wyatt, P.C.

(57) ABSTRACT

A sensing device is provided that includes a tunnel junction created by forming a hole in a layered tunnel junction (for example). A chemically, well-defined surface may be formed by coupling affinity reagents to the electrodes, which, by these means, the surface may be configured to be selective for a particular analyte.

15 Claims, 18 Drawing Sheets

(52) U.S. Cl.
CPC .... *G01N 33/48721* (2013.01); *B01L 2200/10* (2013.01); *B01L 2300/0645* (2013.01); *B01L 2300/0861* (2013.01); *B01L 2300/0887* (2013.01)

(56) References Cited

U.S. PATENT DOCUMENTS

| | | | |
|---|---|---|---|
| 8,961,757 | B2 | 2/2015 | Nuckolls et al. |
| 8,968,540 | B2 | 3/2015 | Reinhart et al. |
| 9,140,682 | B2 | 9/2015 | Lindsay et al. |
| 9,274,430 | B2 | 3/2016 | Gyarfas et al. |
| 9,395,352 | B2 | 7/2016 | Lindsay et al. |
| 9,593,372 | B2 | 3/2017 | Lindsay et al. |
| 9,810,681 | B2 | 11/2017 | Lindsay et al. |
| 2005/0136529 | A1 | 6/2005 | Yang et al. |
| 2005/0239076 | A1 | 10/2005 | Garey et al. |
| 2006/0228717 | A1* | 10/2006 | Joyce .................. B01L 3/5027 435/6.11 |
| 2006/0231419 | A1* | 10/2006 | Barth ...................... B82Y 5/00 205/775 |
| 2009/0084686 | A1 | 4/2009 | Yun et al. |
| 2009/0111117 | A1 | 4/2009 | Chung et al. |
| 2010/0248258 | A1 | 9/2010 | Lee et al. |
| 2010/0289505 | A1* | 11/2010 | Zhang .................. C12Q 1/6869 324/663 |
| 2010/0327874 | A1* | 12/2010 | Liu .................. G01N 33/48721 324/464 |
| 2011/0165572 | A1* | 7/2011 | O'Halloran .......... C12Q 1/6869 435/6.11 |
| 2011/0257504 | A1 | 10/2011 | Hendricks et al. |
| 2012/0125594 | A1 | 5/2012 | Elder |
| 2013/0041132 | A1 | 2/2013 | Brik et al. |
| 2013/0302901 | A1 | 11/2013 | Lindsay et al. |
| 2015/0010935 | A1 | 1/2015 | Pressley |
| 2015/0142327 | A1 | 5/2015 | Ashcroft et al. |
| 2015/0144506 | A1 | 5/2015 | Lindsay et al. |
| 2016/0018384 | A1 | 1/2016 | Lindsay et al. |
| 2016/0025702 | A1 | 1/2016 | Lindsay et al. |
| 2016/0097759 | A1 | 4/2016 | Lindsay et al. |
| 2016/0108002 | A1 | 4/2016 | Zhang et al. |
| 2016/0146828 | A1 | 5/2016 | Lindsay et al. |
| 2016/0177383 | A1 | 6/2016 | Ashcroft et al. |
| 2016/0194698 | A1 | 7/2016 | Lindsay |
| 2016/0258925 | A1 | 9/2016 | Gyarfas et al. |
| 2016/0280723 | A1 | 9/2016 | Zhang et al. |
| 2016/0362384 | A1 | 12/2016 | Zhang et al. |
| 2017/0003245 | A1 | 1/2017 | Lindsay et al. |
| 2017/0016852 | A1 | 1/2017 | Lindsay et al. |
| 2017/0038369 | A1 | 2/2017 | Lindsay et al. |
| 2017/0058336 | A1* | 3/2017 | Ivankin ................ C12Q 1/6869 |
| 2017/0067902 | A1 | 3/2017 | Zhang et al. |
| 2017/0137389 | A1 | 5/2017 | Zhang et al. |
| 2017/0204066 | A1 | 8/2017 | Cohen et al. |
| 2017/0343558 | A1 | 11/2017 | Lindsay et al. |

OTHER PUBLICATIONS

Mok, J. et al., "Digital Microfluidic Assay for Protein Detection" Proceedings of the National Academy of Sciences of the United States of America, 2014, vol. 111, No. 6, pp. 2110-2115.

Zhao, Y. et al., "Single Molecule Spectroscopy of Amino Acids and Peptides by Recognition Tunneling" Nature Nanotechnology 9, pp. 466-473 (2014), Apr. 6, 2014.

* cited by examiner

DIGITAL PROTEIN SENSING CHIP AND METHODS FOR DETECTION OF LOW CONCENTRATIONS OF MOLECULES

CROSS-REFERENCE TO RELATED APPLICATIONS

This application is a U.S. national phase of PCT/US2015/026241, filed Apr. 16, 2015, and claims priority to U.S. provisional application No. 61/980,317 titled DIGITAL PROTEIN SENSING CHIP AND METHODS FOR DETECTION OF LOW CONCENTRATIONS OF MOLECULES", filed Apr. 16, 2014, the entire disclosures of which are incorporated herein by reference.

STATEMENT OF GOVERNMENT INTEREST

This invention was made with government support under R01 HG006323 awarded by the National Institute of Health. The government has certain rights in the invention.

BACKGROUND

FIG. 1 shows a plot of the concentration of known proteins in cells versus the total number of known proteins (Archakov, A. I., Y. D. Ivanov, A. V. Lisitsa, and V. G. Zgoda, *Afm Fishing Nanotechnology Is the Way to Reverse the Avogadro Number in Proteomics*. Proteomics, 2007. 7: p. 4-9). Extrapolation of the known data to low concentrations suggests that there are many more unknown proteins present at concentrations well below the current detection limit. This limit is set by the smallest dissociation constant of affinity reagents used to collect proteins from cell extract or serum, and these are typically nM at best. In order to collect proteins at much smaller concentrations, large amounts of sample are generally required, together with a multitude of affinity reagents, so that binding by a very small fraction (e.g., when the concentration of sample is much less than $K_d$) provides a useable amount of sample.

Digital detection may be used to individually count captured molecules resulting in increased sensitivity. This has been demonstrated by Mok et al. (Mok, J., M. N. Mindrinos, R. W. Davis, M. Javanmard, *Digital Microfluidic Assay for Protein Detection*. Proc Natl Acad Sci USA, 2014. 111: p. 1323998111) via a "lab-on-a-chip" in which captured analytes are each tethered to a bead, where each bead is subsequently detected individually via a corresponding electrical signal in a narrow channel.

SUMMARY OF THE DISCLOSURE

Accordingly, some of the embodiments of the present disclosure can be configured to detect binding events of a minute fraction of a population of affinity reagents. In some such embodiments, this may be accomplished by, for example, direct electrical detection of individual molecules, and may also be done in a time resolved manner (for example). Thus, in some embodiments, even if only one affinity reagent among a large population is bound, the event can be detected, and in some embodiments, it may be detected even if bound for just a short amount of time.

In some embodiments, digital detection may be provided which may be used to lower the concentration detection limit down to a minute fraction of $K_d$. Furthermore, because detection in some embodiments is carried out via a nanoscale device at a single molecule level, the total amount of sample required may be greatly reduced as compared to conventional approaches (e.g., ELISA, mass spectrometry). Moreover, because a binding event(s) generates a direct electrical signal characteristic of the analyte, in some embodiments, labeling or secondary probes are not required.

In some embodiments, a sensing device is provided that includes a tunnel junction created by forming a hole in a layered tunnel junction (for example). A chemically, well-defined surface may be formed by coupling affinity reagents to the electrodes, which, by these means, the surface may be configured to be selective for a particular analyte.

Some embodiments of the present disclosure provide a readily manufacturable platform for monitoring, for example, molecule binding events between an affinity reagent and a target molecule (and in some embodiments, a single binding event). Dynamic information obtained from such embodiments may be used to extend detection capability down to concentrations that may be orders of magnitude below the $K_d$ of the affinity reagent.

In some embodiments, a device for detecting the binding of a molecule to a cognate ligand is provided which may comprise a first planar electrode having a length, a width and a thickness, an insulating layer having a length, a width and a thickness, the insulating layer covering a substantial portion of the first electrode, and a second planar electrode having a length, a width and a thickness, and arranged adjacent to the insulating layer. The insulating layer may be configured to be sandwiched between the first and second electrodes, and the second electrode may be configured with a width that is less than the width of the first electrode. The device may also include an opening through the electrodes configured to expose the gap between them and establishing an electrodes-insulating layer junction, where the opening is spaced away from the perimeter of each electrode, one or more recognition molecules comprising a cognate ligand, a chemical group configured to couple the cognate ligand to at least one of the electrodes, and a reference electrode in communication with at least one of the electrodes.

In some embodiments, the reference electrode is configured with a substantially constant potential difference with respect to at least one of the electrodes. In addition, the cognate ligand may comprise at least one of an antibody, a Fab fragment, an aptamer and a peptide configured to bind to one or more protein targets.

In some embodiments, the device is configured to detect single molecular binding events corresponding to low concentration sample solutions, and may also be configured for sequencing a peptide chain.

In some embodiments, a system for detecting the binding of a molecule to a cognate ligand is provided and may comprise one and/or another of devices for detecting binding events as disclosed herein, and purification means for purifying a patient serum sample for obtaining one or more target proteins. Such purification means may comprise, for example, a lab-on-a-chip (e.g., as disclosed herein).

In some embodiments, a method for detecting at least one binding event between a recognition molecule and a target molecule is provided, which may comprise providing one and/or another of detecting devices disclosed in the present disclosure, providing a substantially fixed bias between the electrodes, flowing a sample solution adjacent to the junction, recording current signals generated as a result of one or more binding events between one or more molecules in the sample and corresponding recognition molecules, and determining at least one of a number and type of molecules present in a sample solution based on the characteristics of the signal generated as each type of molecule binds.

The characteristics of the signal may comprise at least one of baseline current, peak current above a baseline, peak width, peak shape as encoded by Fourier, wavelet or Cepstrum component amplitudes, and flatness of the peak top expressed as root mean square signal variation.

Some method embodiments may further include recording at least one of the number and type of molecules determined.

Some method embodiments may further comprise at least one of recording and counting signals generated by single molecule binding events of a plurality of protein variants contained in the sample solution.

At least some of the embodiments provide a platform which may be readily configured to sequence proteins, for example, using methods outlined in international patent application no. PCT/US2013/024130, entitled, "System apparatuses and methods for reading an amino acid sequence," hereby incorporated by reference.

In some embodiments, a system for generating a target molecule includes a first channel configured to receive a sample. The sample includes cells, and the cells contain a biomolecule. The first channel includes antibodies for capturing the cells in the sample, and the first channel is further configured to receive a lysis buffer for lysing the captures cells to generate a lysate. The system also includes a second channel fluidly coupled to the first channel. The second channel is configured to receive the lysate and is functionalized with antibodies for binding the biomolecule in the lysate. The second channel is further configured to receive an eluting solution to generate an elution buffer including the biomolecule. The system also includes a third channel fluidly coupled to the second channel. The third channel is configured to receive the elution buffer including the biomolecule and is further configured to fragment the biomolecule to generate a solution including the target molecules.

In some embodiments, a system includes a first recognition tunneling electrode configured to interface a first reservoir during use. The system also includes a second recognition tunneling electrode coupled to the first recognition tunneling electrode. The system also includes a dielectric substrate coupled to the second recognition tunneling electrode. The dielectric substrate is configured to interface a second reservoir during use. A nanopore is formed through the first recognition tunneling electrode, the second recognition tunneling electrode, and the dielectric substrate, and is configured to fluidly couple the first reservoir and the second reservoir. The system also includes a bias voltage source configured to establish a voltage bias between the first recognition tunneling electrode and the second recognition tunneling electrode. The system also includes a current monitor configured to generate a recognition tunneling signal when a molecule passes adjacent to or through the nanopore.

In some embodiments, a system includes a first microfluidic device, the first microfluidic device including a first microfluidic channel. The first microfluidic channel including a first inlet port and a first outlet port. The system also includes a first recognition tunneling electrode configured to interface the first microfluidic device. The system also includes a second recognition tunneling electrode coupled to the first recognition tunneling electrode. The system also includes a second microfluidic device, the second microfluidic device including a second microfluidic channel. The second microfluidic channel includes a second inlet port and a second outlet port. A nanopore is formed through the first microfluidic channel, the first recognition tunneling electrode, the second recognition tunneling electrode, and the second microfluidic channel. The nanopore is configured to fluidly couple the first microfluidic channel and the second microfluidic channel. The system also includes a bias voltage source configured to establish a voltage bias between the first recognition tunneling electrode and the second recognition tunneling electrode. The system also includes a current monitor configured to generate a recognition tunneling signal when a molecule passes adjacent to or through the nanopore.

These and other embodiments of the present disclosure, as well as objects and advantages of one or more thereof, will become event more evident with reference to the attached drawings and detailed description which follows.

DETAILED DESCRIPTION OF SOME OF THE EMBODIMENTS

Figure 1:
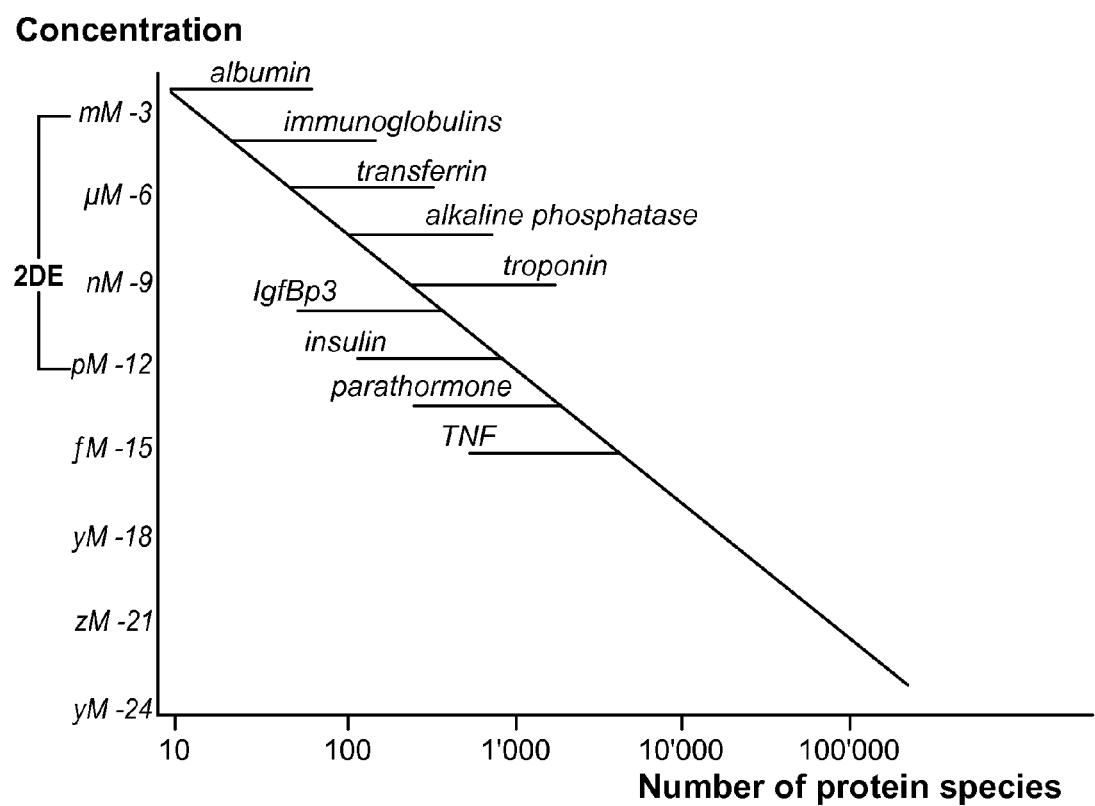
FIG. 1 illustrates a plot of the concentration of proteins in vivo versus the number of protein species at a given concentration.
Figure 2:
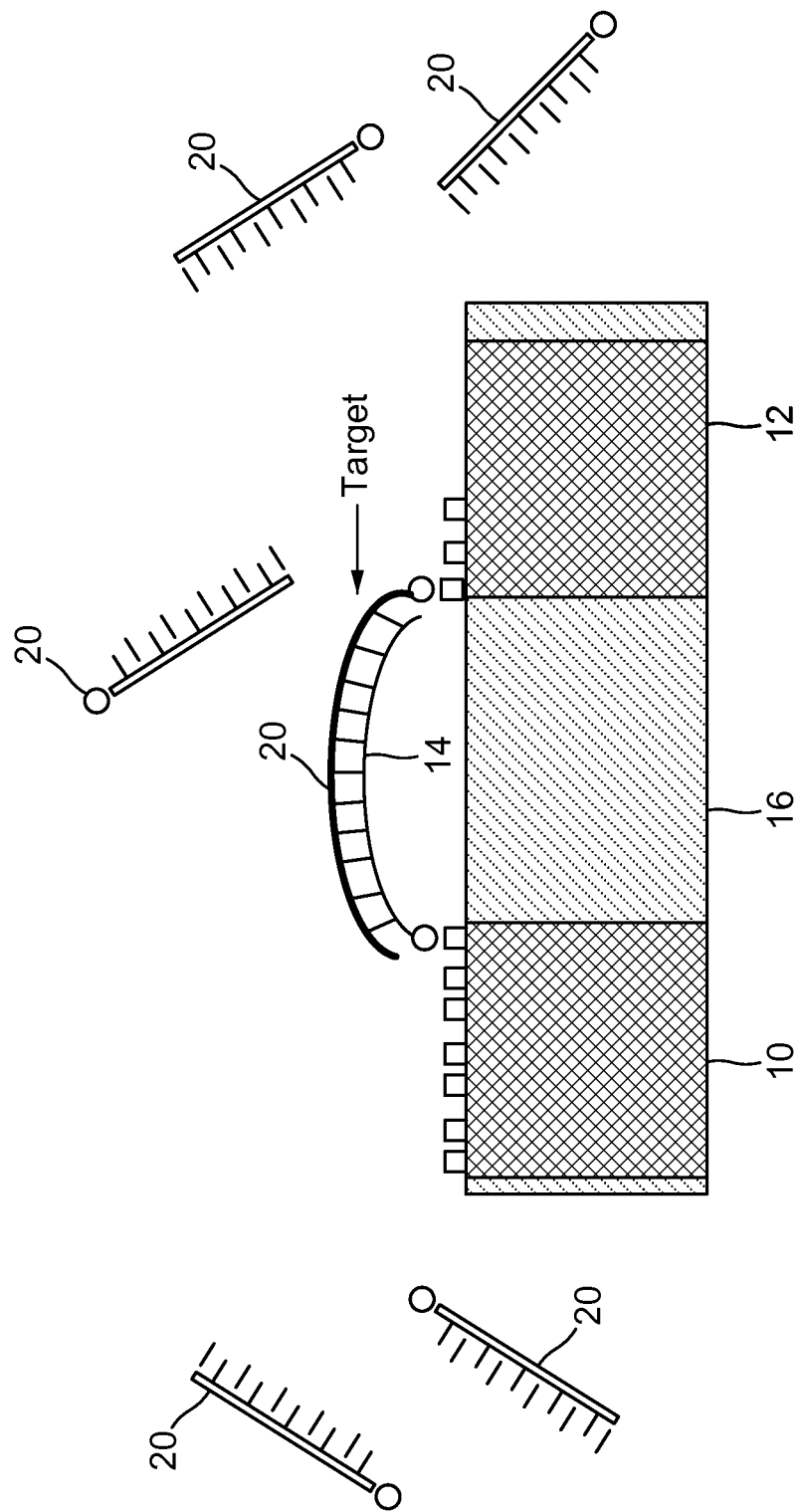
FIG. 2 illustrates a prior art device of Pishrody et al. (Pishrody, S. M., S. Kunwar, and G. T. Mathai, Electronic Detection of Biological Molecules Using Thin Layers, U.S. Pat. No. 6,824,974 B2 Nov. 30, 2004).
Figure 3:
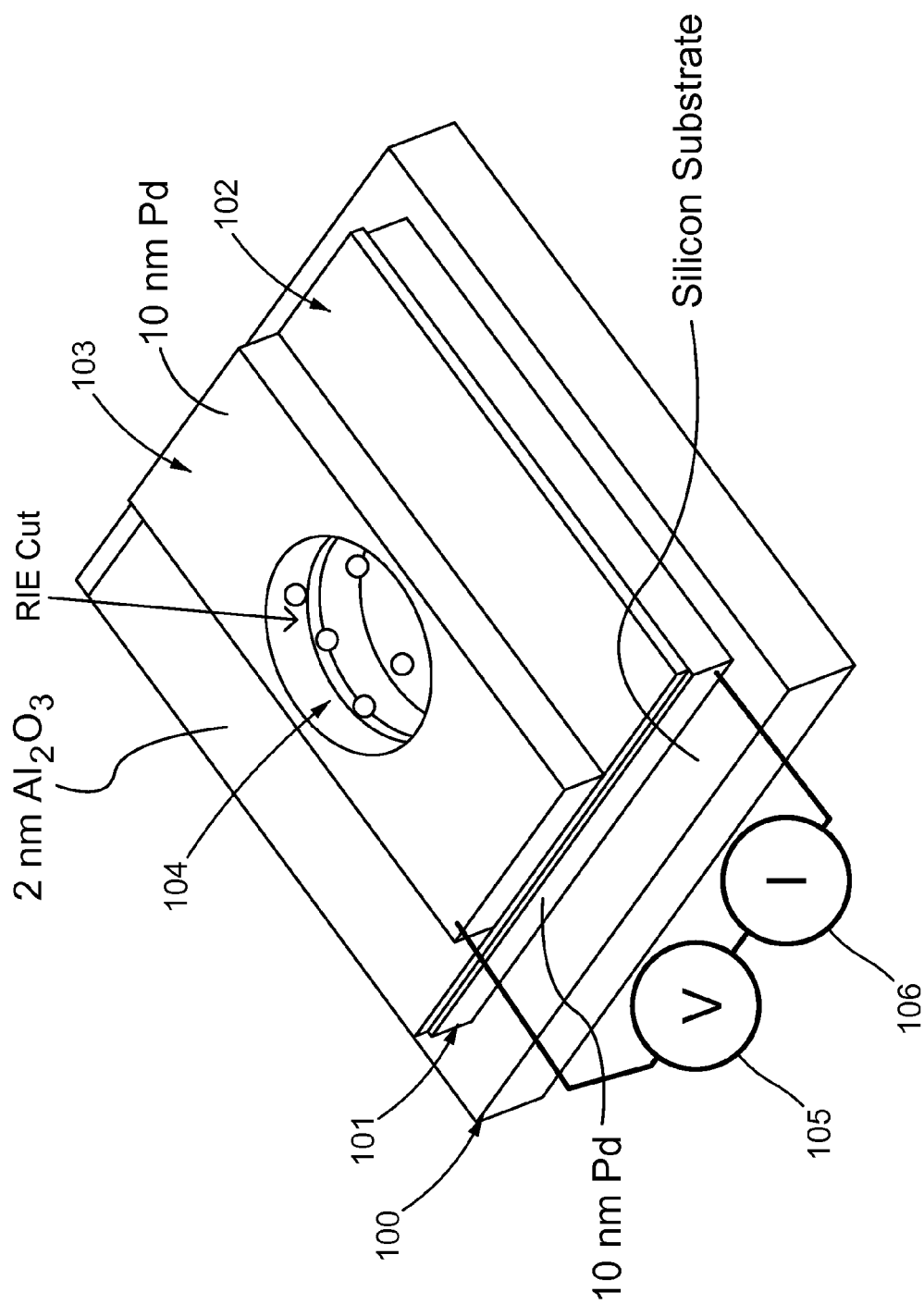
FIG. 3 illustrates a device according to some of the embodiments of the present disclosure.
Figure 4:
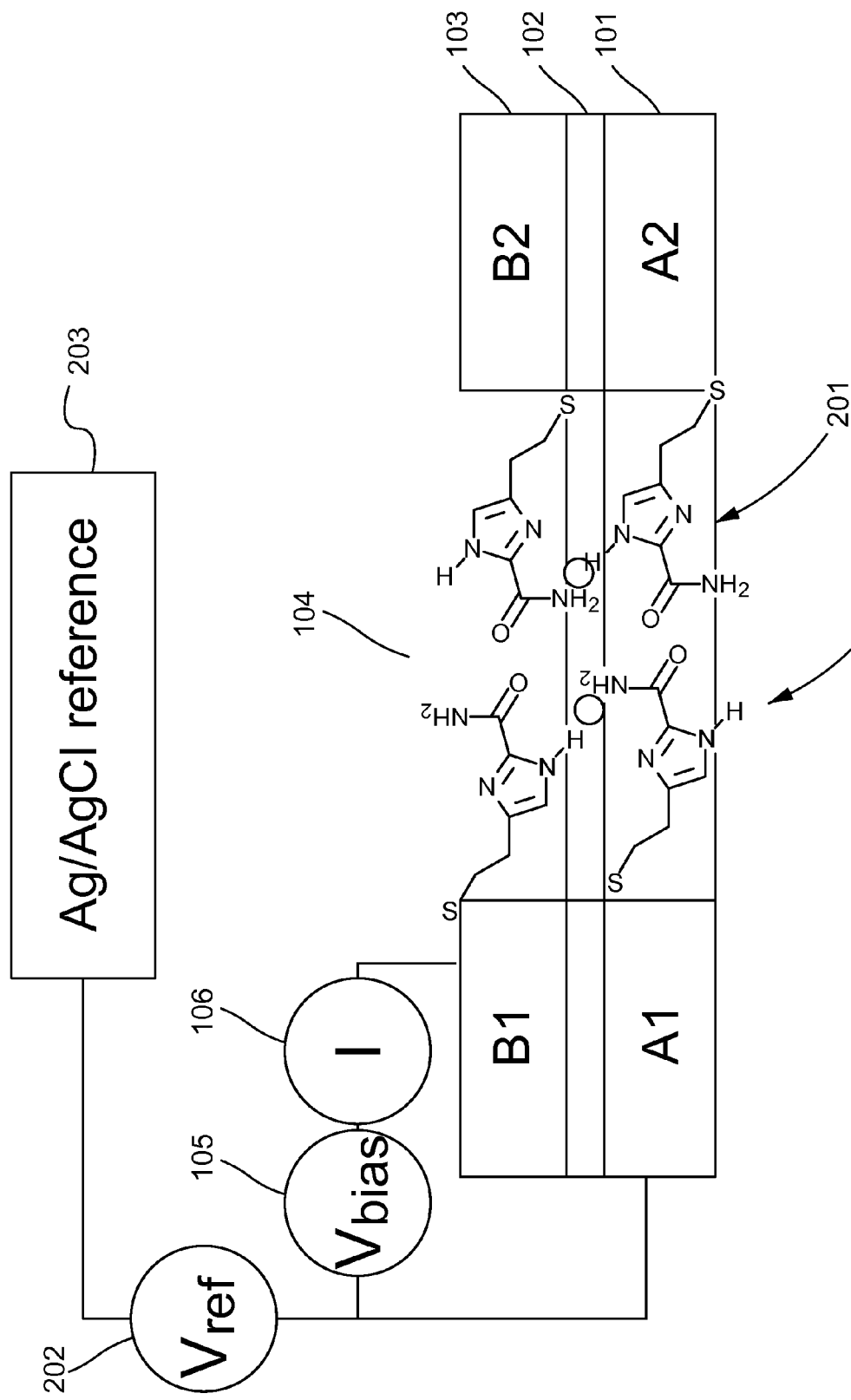
FIG. 4 illustrates a system according to some embodiments, which shows connection of biasing components and a reference electrode(s), as well as illustrating the surface of the electrodes functionalized with the ICA reader molecules (for example).

FIG. 3 illustrates a device according to some of the embodiments of the present disclosure. An example of the biasing and reference electrode configuration and connection, which may be used with such disclosed devices, is illustrated in FIG. 4.

Referring to FIG. 3, a device according to some embodiments of the disclosure (which may also be referred to as a tunneling device), may be constructed by deposition of a layer of Pd 101, or similar noble metal, of about 10 nm thickness over/on an adhesion layer, which may be about 1 nm Ti on at least one of a silicon or silicon nitride support 100. This layer can cover an area of many microns (e.g., about 1×1 micron up to about 100×100 microns) on each side, though, in some embodiments, the particular dimensions may not be important in the plane of the device. In some embodiments, the electrodes can be greater than 10 nm in thickness (portions of the electrode spaced away from the junction by more than 1 to 100 nm may not contribute to the signal), with some embodiments including a thickness of less than about 500 nm may be used.

Figure 5:
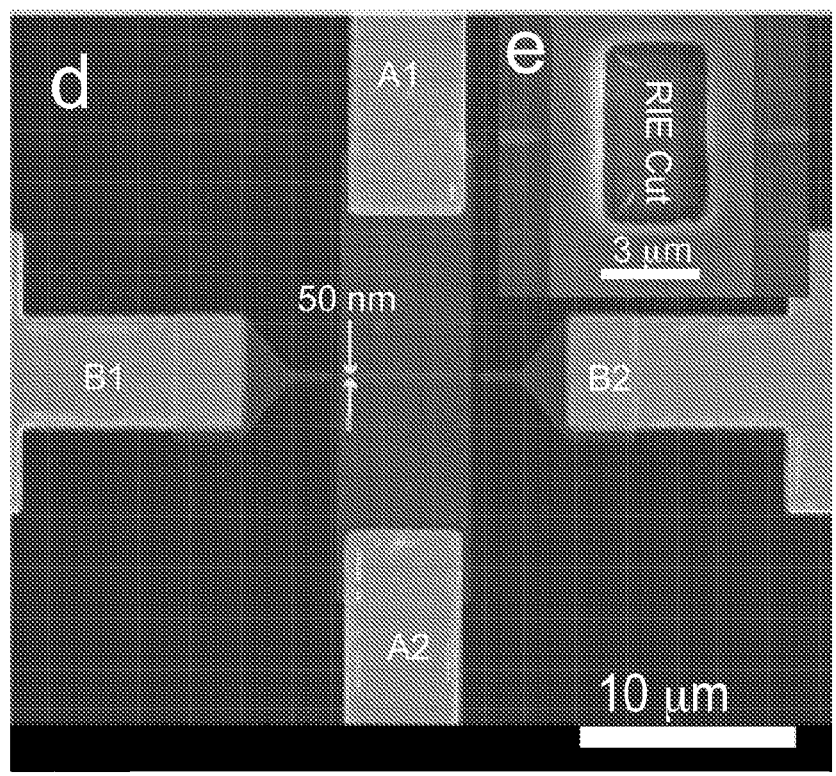
FIG. 5, main panel: a scanning-electron microscope (SEM) image of a top view of a device according to some embodiments; insert (e) illustrates a trench cut into the center region where electrodes intersect (according to some embodiments).

The support may comprise any generally flat support surface/substrate, including a semiconductor wafer surface or a glass surface, or a mica surface. In some embodiments, a first electrode (which may also be referred to as a lower metal electrode) may comprise a strip of about 5 microns in width, contacted at each end by, for example, gold wires (A1 and A2 in FIG. 5), although any metallic material/contact to connect with the electrode may be used.

In some embodiments, a majority of the lower portion of the device may be covered with a dielectric material (i.e., insulating) layer 102 of between about 2 nm to about 3 nm thick. The dielectric material may be deposited by, for example, atomic layer deposition. In some embodiments, the entire lower portion of the device may be completely covered with the dielectric. Any dielectric material may be used, including oxides of silicon and other semiconductors and oxides of metals, including Hafnium Oxide. In some embodiments, dielectric layers thicker than 2 to 3 nm may be used when seeking larger target molecules (example embodiments may include a dielectric layer of between about 1 nm to about 50 nm.

On the surface of the deposited layer of $Al_2O_3$, a Pd (or similar metal) wire 103 of less than about 100 nm width, may be deposited. While any metal will perform the required function of the wire 103 the noble metals, Au, Pt, Pd, Rd, Ag, Os, Ir are preferred. In some embodiments, this top wire is configured with the noted range of width, for at least one of the following reasons. Firstly, the edges do not contribute signals because the edges of the top 103 and bottom 101 electrodes are well separated by the film of $Al_2O_3$ or other dielectric. Thus, signals can be limited to an area of the device that is opened deliberately as described below. Secondly, tunnel junctions can be produced at high yield, since a narrow top electrode may be less likely to contain an area with pinholes through the dielectric layer 102. Accordingly, in some embodiments, a wire of less than about 500 nm in width may be preferable. The quality of the tunnel junction formed between the electrodes 101 and 103 may be evidenced by measuring current 106 when a voltage 105 is applied across the device.

Figure 6:
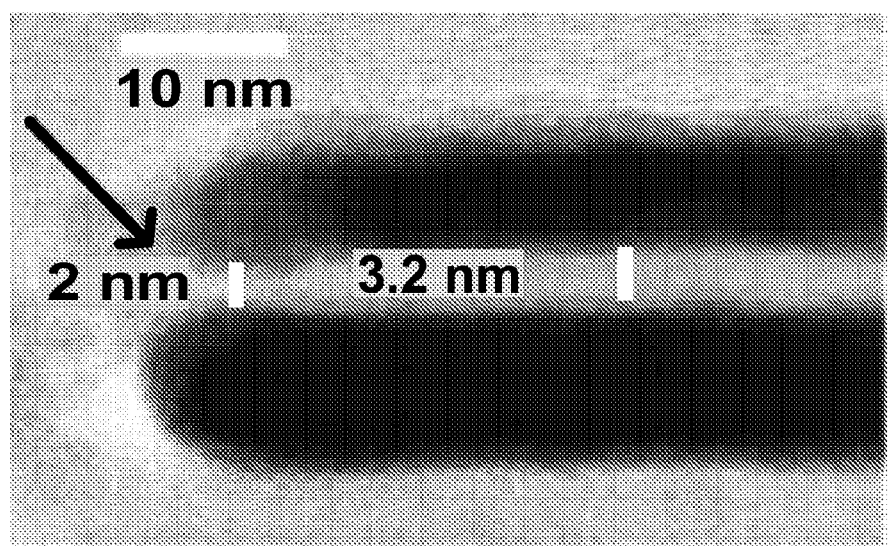
FIG. 6 illustrates a tunneling-electron microscope (TEM) cross section of a tunnel junction edge according to some embodiments, which shows a 2 nm (for example) sensing gap (a slice of the junction was lifted out, e.g., using focused ion beam milling, to take this image).

In some embodiments, in order to expose the edges of the electrodes, which may be referred to as the tunneling junction, to the solution containing analyte molecules, a hole 104 is cut through the structure using, for example, reactive ion etching (RIE). In some embodiments, this may be carried out using $Cl_2$ gas to etch the palladium and $BCl_3$ gas to etch the $Al_2O_3$. A TEM cross section through the edge of the exposed tunnel junction, taken by milling out a slice with a focused ion beam, is shown in FIG. 6, which clearly illustrates a 2 nm separation of the electrodes at the edge of the junction (according to some embodiments). A top down view of the region cut away by RIE is shown in the inset on the upper right (e) in FIG. 5.

In some embodiments, the device may be covered with a layer of PMMA, which is opened (e.g., via lithography) over the hole and a microfluidic channel may be positioned such that analyte can be delivered to the tunnel junction.

Figure 7:
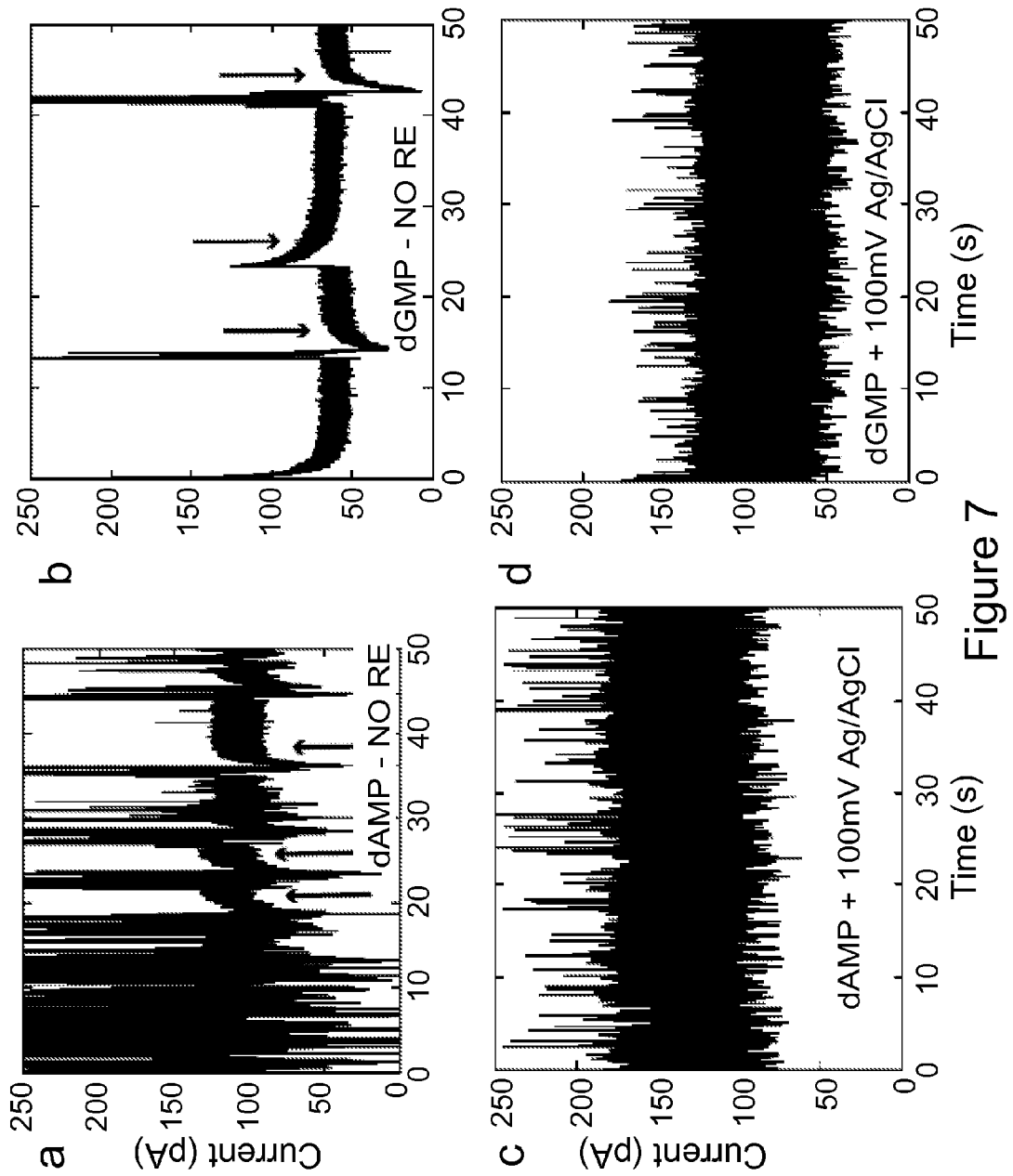
FIG. 7 illustrates collected signals without (a, b) and with (c, d) a reference electrode connected to a device according to some embodiments.

Referring to FIG. 4, the lower electrode 101 may be connected to a reference electrode (shown here as Ag/AgCl reference, 203) which may be held at a bias $V_{ref}$ 202 with respect to lower electrode 101. Thus, the top electrode 103 may be at a potential of $V_{ref}+V_{bias}$ with respect to the reference electrode. By holding electrode 103 positive of zero volts versus Ag/AgCl, the lower electrode 101 may be kept away from instabilities cause by adsorption of negative charges which could move the electrode into a region where hydrogen evolution occurs. Values of $V_{ref}$ for Pd electrodes, in some embodiments, may be between 0 to +200 mV, with 100 mV being commonly used. The effect of the reference electrode, in some embodiments, is to stabilize the device, and example of which is illustrated in FIG. 7. As shown, panels a and b show signals taken with DNA nucleotides dAMP (a) and dGMP (b) without a reference electrode. Accordingly, large swings in current, and regions where no signal occurs, are consequences of the electrochemical instability of the device. However, in some embodiments, upon connecting a reference electrode to the device (e.g., to the top electrode 103), panels d and e, the device is stable, and can produce trains of reproducible signal for times that usually exceed an extensive period of time (e.g., 5 hours).

Figure 8:
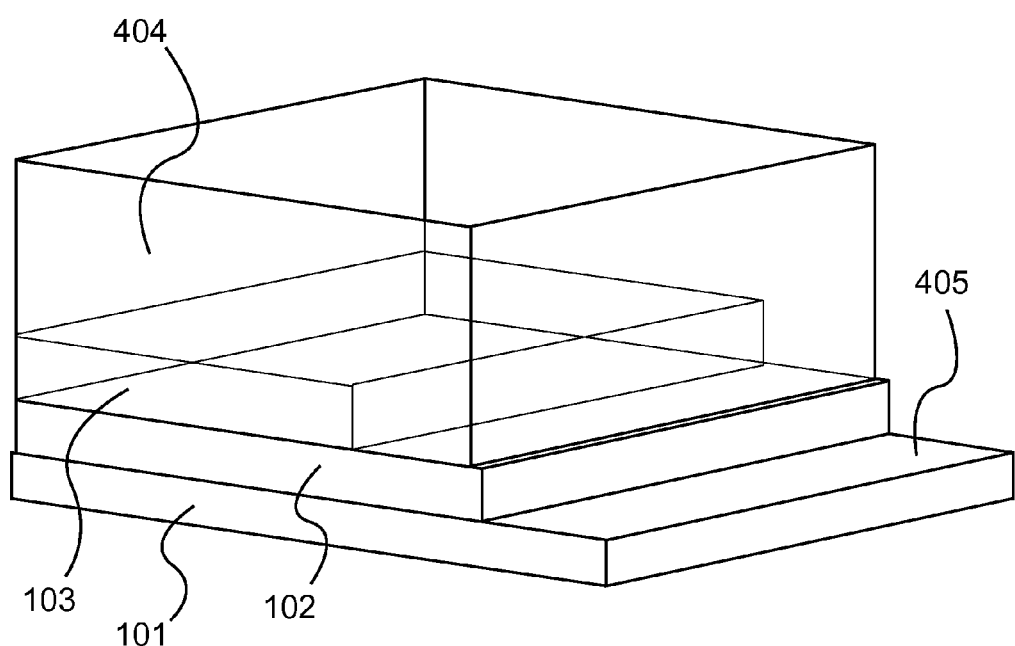
FIG. 8 illustrates a method for forming a quasi-reference, according to some embodiments, by extending the lower electrode so that it contacts the fluid.

The reference may be any of the standard reference electrodes placed in contact with the solution that carries the molecules to the junction. Examples include, for example, Ag/AgCl as shown in FIG. 4, a saturated calomel electrode, and a hydrogen electrode. Such electrodes have an advantage that the electrochemical processes (e.g., for devices according to some embodiments) can be related to a standard potential scale, useful in interpreting signals from the device. However, it is not essential for stable operation of the device. All that is required, in some embodiments, is a connection to an electrode of relatively constant polarization (e.g., a "quasi reference") where the relationship of the electrode potential to standard scales (such as the normal hydrogen scale) is not known. However, a quasi-reference is easier to implement. A quasi reference may be any large electrode area in contact with the solution. Accordingly, if the interfacial capacitance is very large compared to that of the device electrodes (e.g., pF or more), than the quasi reference may not change potential significantly as molecules are adsorbed from the solution. FIG. 8 shows one way to implement this on the device itself. As shown, portions of the device away from the tunnel junction may be passivated with a layer of insulator 404, typically PMMA, that has been patterned to expose the junction. Lower electrode 101 is shown extending out of the insulated region 404 to leave a large area 405 exposed to contact the electrolyte carrying the target molecules. In some embodiments, the quasi reference may be made by extending the lower Pd electrode, but any suitable metal could used for this function, including Ag, Au, Pt, Ir, Rd (for example).

Current spikes are shown in FIG. 7 for an exemplary device and target molecules/analytes, according to some embodiments, which may be produced when the electrodes are functionalized with a layer of recognition molecules (201 in FIG. 4). In the noted example, the recognition molecules are 4(5)-(2-mercaptoethyl)-1H-imidazole-2-carboxamide (ICA). When the analyte concentration is reduced to a low enough value (e.g., about 10 nM for the DNA nucleotide dAMP), the complex signals resolve into reproducible spikes of current that sit on top of a background current signal. An example is given in FIG. 9, in this case for 10 nM solution of dAMP in 1 mM phosphate buffer, pH=7.0.

Figure 10:
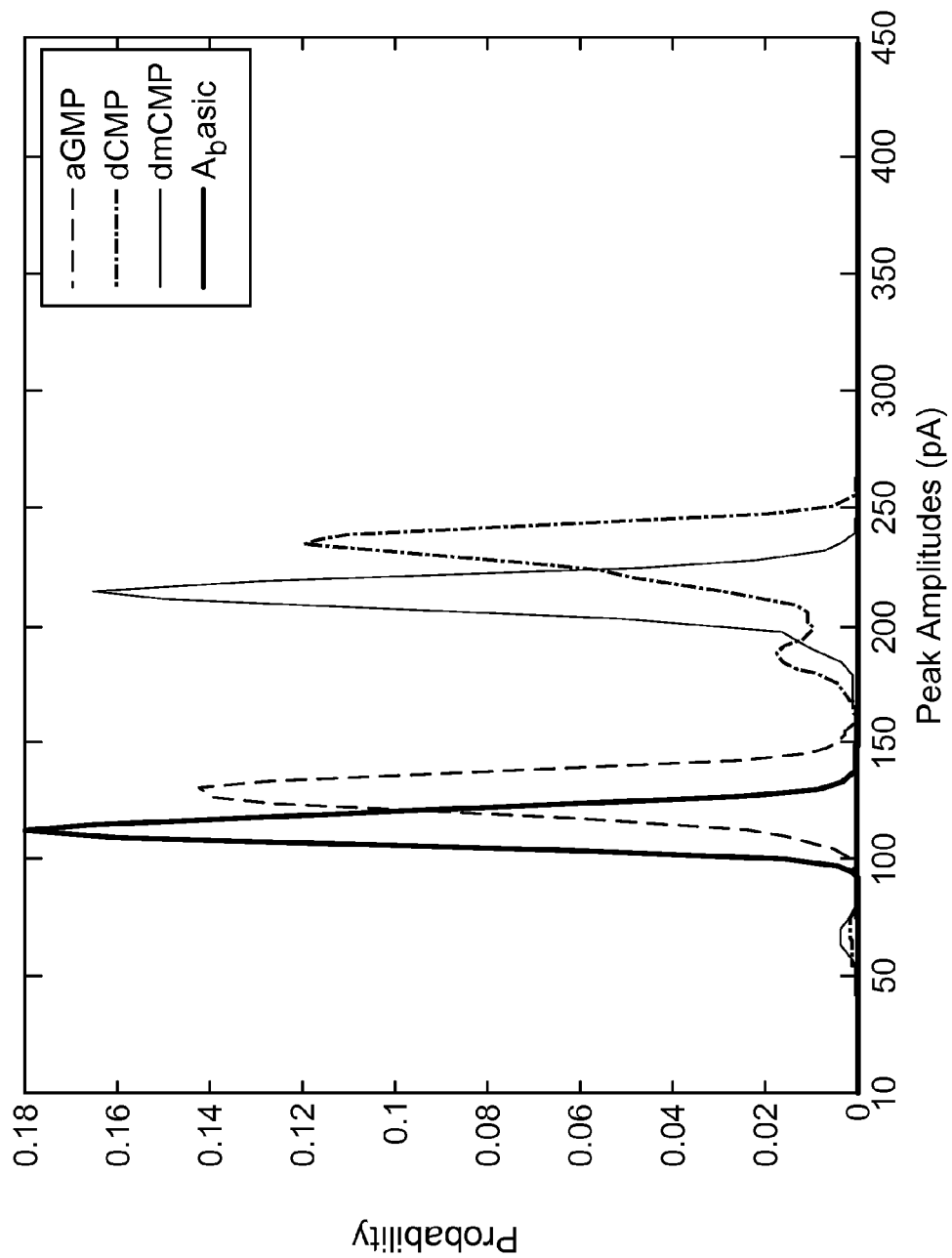
FIG. 10 illustrates distributions of current peak values for dGMP, dCMP, dmCMP (5-methyl cytosine monophosphate) and a basic nucleotide at low (10 nM) concentrations, according to some embodiments of the present disclosure.
Figure 11:
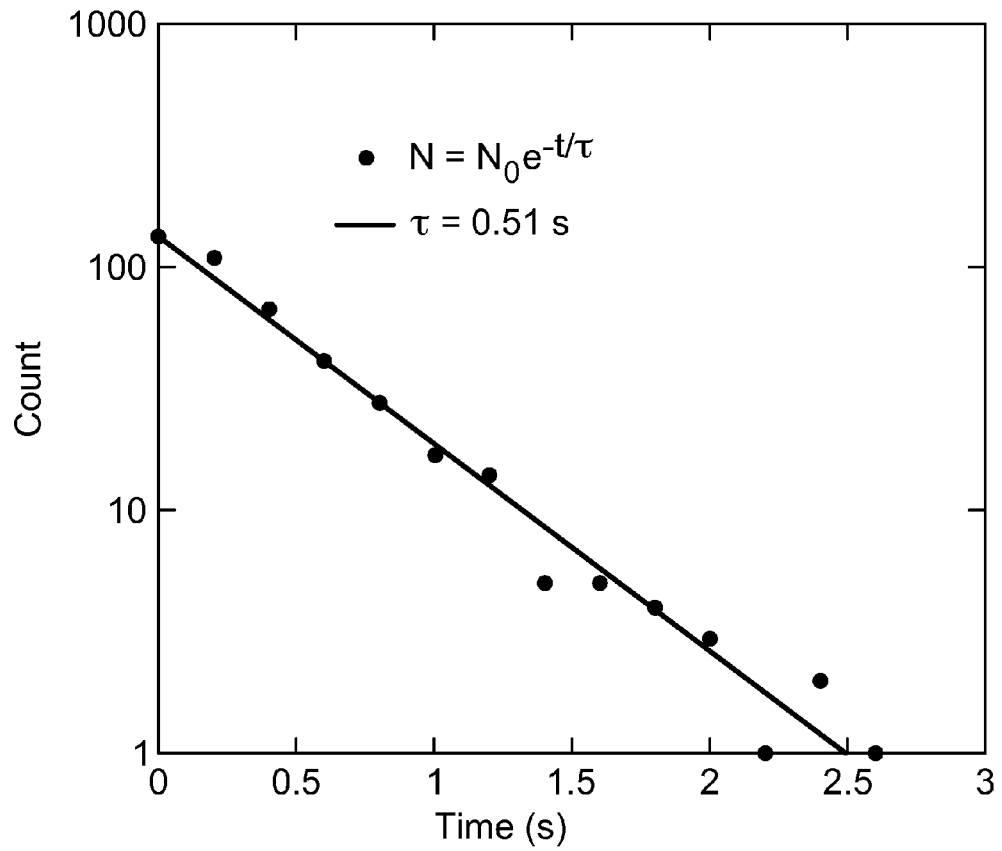
FIG. 11 illustrates a plot of the distribution of start times of current spikes at low concentrations, as detected by some embodiments, illustrating an exponential distribution for single molecule events.

The current background is about 30 pA and the spikes positioned on top of background reach about 90 pA. The distribution of signals may be narrow, as shown for dGMP, dCMP, d(5-methylCMP) and an a basic nucleotide in FIG. 10. Furthermore, according to such embodiments, the interval between the arrival of successive peaks, is exponentially distributed (FIG. 11), which is illustrative of single-molecule origin of these spikes.

Figure 12:
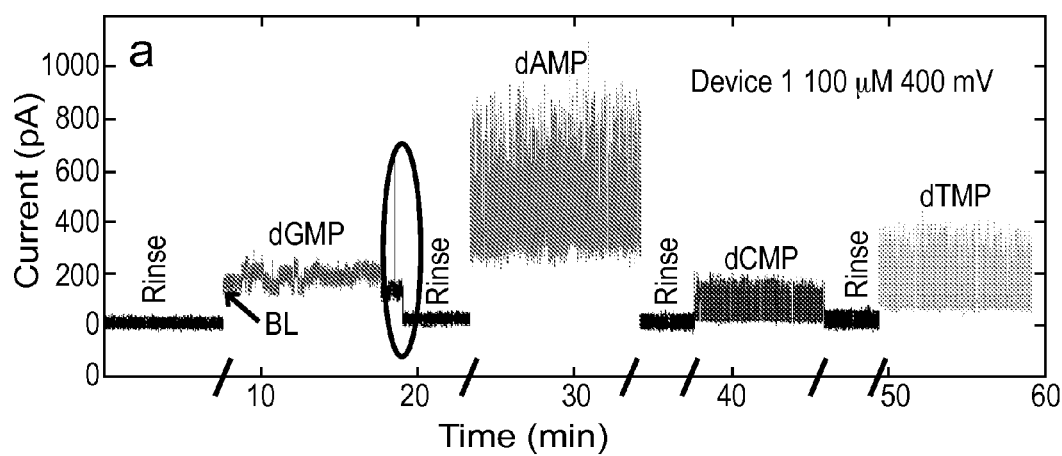
FIG. 12 illustrates a signal train from a detection device according to some embodiments as the four DNA nucleotides are flushed through with rinses in between; the signal comprises a baseline current (BL) and noise spikes, both of which are chemically-sensitive.
Figure 13:
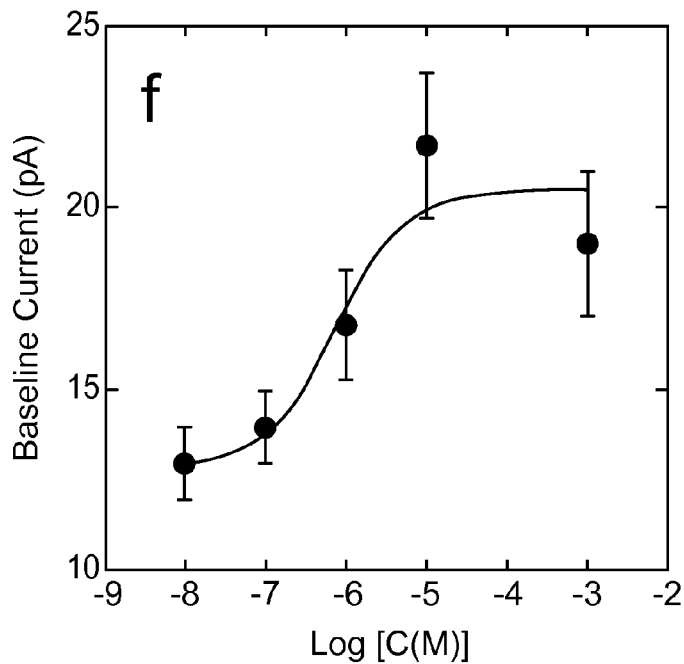
FIG. 13 illustrates baseline current vs. analyte concentration, with respect to some embodiments of the present disclosure, with the solid line being a fit to the Hill-Langmuir isotherm (equation 1).

The baseline current signal may also contain chemical information. FIG. 12 shows a current trace for micromolar concentrations of the four nucleotides, dGMP, dAMP, dCMP and dTMP upon being flowed through a device according to some embodiments. As shown, at each rinse with buffer alone, the baseline signal disappears, and the baseline is different for each analyte. The baseline signal increases with analyte concentration (FIG. 13), thus representing specific chemical effects on the tunnel junction current caused by adsorption of the analyte molecules.

Figure 14:
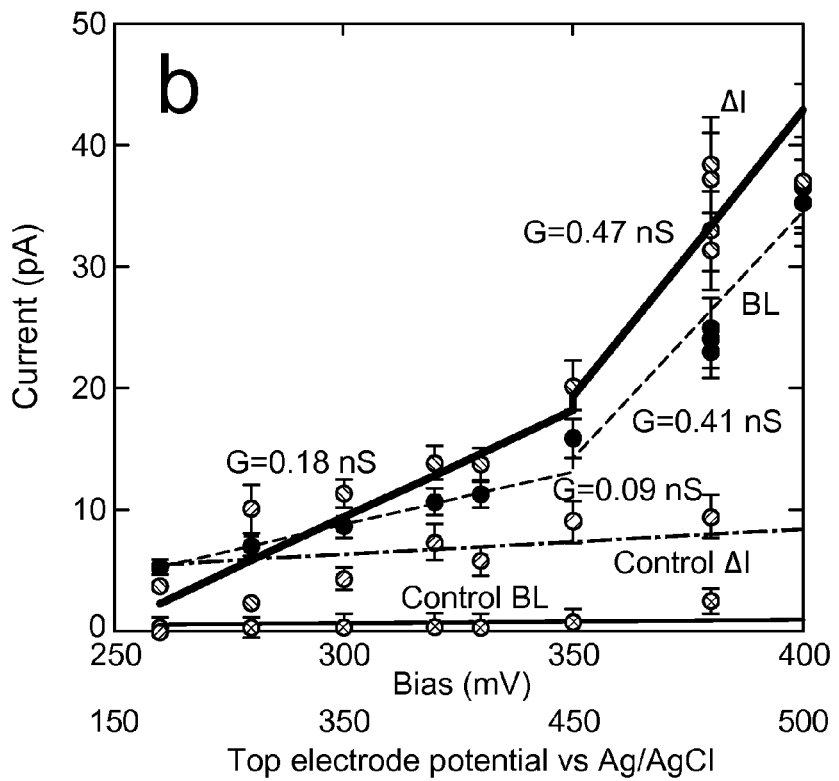
FIG. 14 is a plot of current spike height ($\Delta I$) and baseline current (BL) vs. bias for a sample of 10 nM dAMP as determined by some embodiments of the present disclosure. Controls using the buffer solution alone are shown in the lower two curves. Conductance of the device increases abruptly at 350 mV bias which is 450 mV vs Ag/AgCl at the top electrode 103, given that the bottom electrode 101 (see FIG. 3) was held at +100 mV vs Ag/AgCl. The scale directly beneath the plot indicates the bias across the device, while the lower scale indicates the potential of the top electrode with respect to the Ag/AgCl reference.

In some embodiments, the signals, which may include both the current spikes and the baseline, have a non-linear dependence on $V_{bias}$ as shown in FIG. 14. As shown, both the baseline signal (BL) and the spikes (ΔI) increase in amplitude more rapidly with voltage when the potential of the top electrode (103) exceeds 450 mV vs. Ag/AgCl. Thus, the same electrochemical change may affect both the process that gives the spikes and the process that gives the baseline. Cyclic voltammetry shows that this potential on the Ag/AgCl scale corresponds to a reversible oxidation of the ICA reader molecules. Thus, the current path in both cases (baseline signals and signal spikes on top of the baseline) is via the ICA reader molecules.

Figure 9:
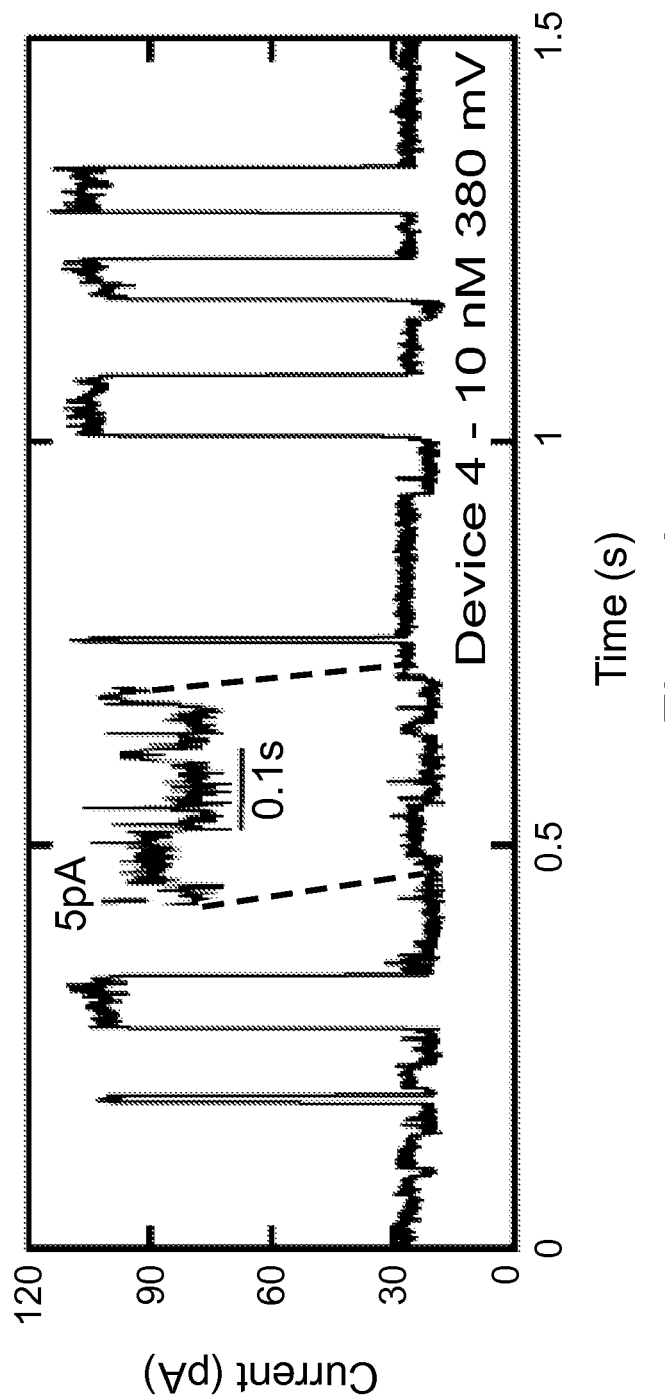
FIG. 9 illustrates recognition signals at low concentration of analyte, according to some embodiments; current spikes that go up to 90 pA correspond to molecules binding a pair of recognition molecules such that the tunnel gap is bridged, while the background (30 pA) current comes from binding events to just one electrode.
Figure 15:
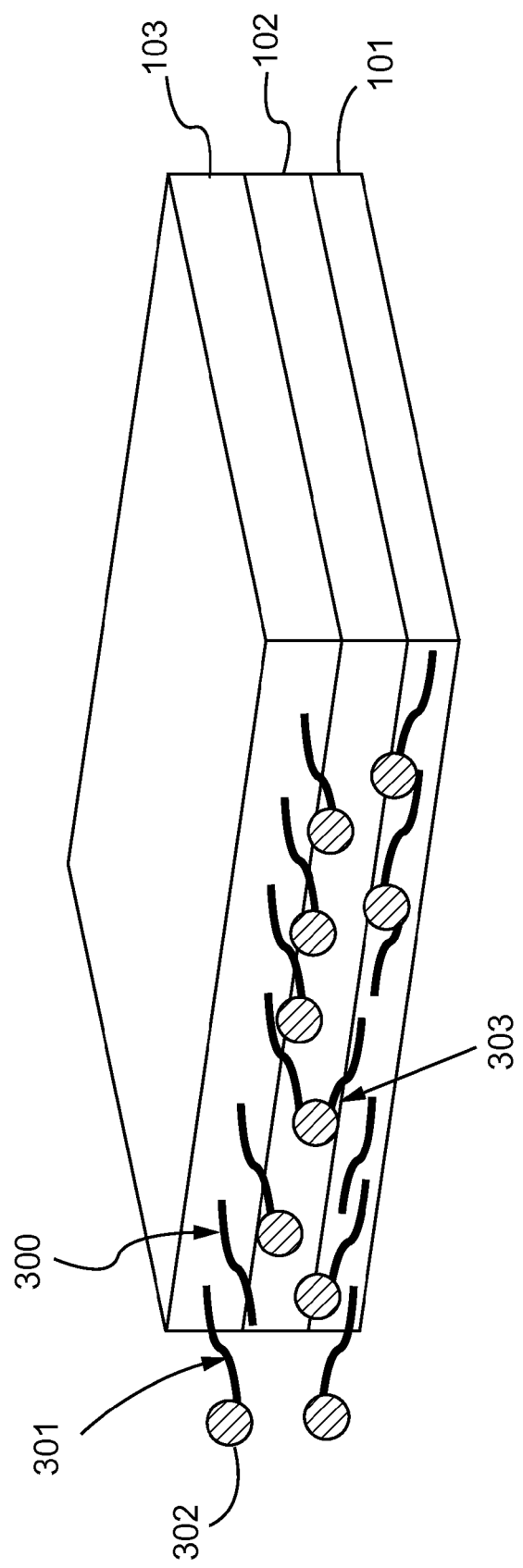
FIG. 15 illustrates types of binding that generate the signal spikes and the background current, according to some embodiments of the disclosure.

Inspection of the background current at low concentration of analyte is illustrated in FIG. 9, which shows discrete steps in the signal (enlarged in the inset), which provides support that, in some embodiments, the background may be the sum of many single molecule processes. In these embodiments, the baseline current increases with adsorption of analyte molecules as the concentration is increased (FIG. 13), and also when the reader molecule (201 in FIG. 4) is oxidized, providing support that the signal corresponds to the attachment of analyte molecules to the reader molecule. Referring to FIG. 15, 300 shows a reader molecule and 301 shows a reader molecule with an attachment to an analyte molecule 302. On occasion, a reader molecule is aligned on each electrode such that an analyte molecule can be bound in a manner (303) that provides a conducting path between the two electrodes 101 and 103. Accordingly, quantum mechanical calculations provide evidence that the type of connection shown in 303 is responsible for the larger current spikes in FIG. 8 (of 90 pA amplitude). The multitude of other types of binding, like those shown as 301, combine to provide the background signal. It is a feature according to some such embodiments, that the background signal may be, itself, chemically sensitive and generates signals of high frequency with much smaller concentrations than those that give the bigger spikes generated by the rarer attachments like those illustrated as 303.

For example, in some embodiments, increased sensitivity of detecting binding events may be illustrated by providing a device having two electrodes, each of 10 nm height and 50 nm width, the total electrode area presented to the solution is 1000 $(nm)^2$. Each reader molecule occupies about 1 $(nm)^2$, thus providing about 1000 reader molecules on the electrodes. Clearly, in such embodiments, the binding of just one molecule may be readily detectable. Thus, it is straightforward to configure a device according to some embodiment to detect the binding of about 0.1% of the available sites. Furthermore, in some embodiments, even if the site is occupied for just a fraction of time, electrical signals are detected. For example, an event of 1 ms duration is readily detectable, as shown by the signals in FIG. 9. In such embodiments, assuming that the device is operated for 1 second, it may therefore be possible to detect binding that occurs for only 1 part in 1000 of the observation time.

One of skill in the art will appreciate that according to such embodiments, when taken together with the ability to observe events like this from just 1 in $10^3$ molecules, a binding fraction of 1 part in $10^6$ generates a readily detectable signal. As an example, suppose that the reader molecule is an affinity element, e.g., an antibody, Fab fragment, aptamer or peptide, with a $K_d$ of 1 nM. This would correspond to a $K_d$ value for a particularly good antibody, although a poor cognate ligand will have a $K_d$ of 100 nM or better. Fractional coverage θ of the electrode surface is given by the Hill-Langmuir isotherm:

$$\theta = \frac{C/K_d}{1 + C/K_d} \quad (1)$$

where C is the concentration of analyte molecules. In equation (1), θ implies that, with $K_d$~1 nM, a concentration as small as $10^{-15}$ M would yield one 1 ms event per second. A $K_d$ of 100 nM would yield one event every 100 s. This represents an enormous increase in sensitivity compared to current techniques, where nM concentrations are typically the lower limit.

Figure 16:
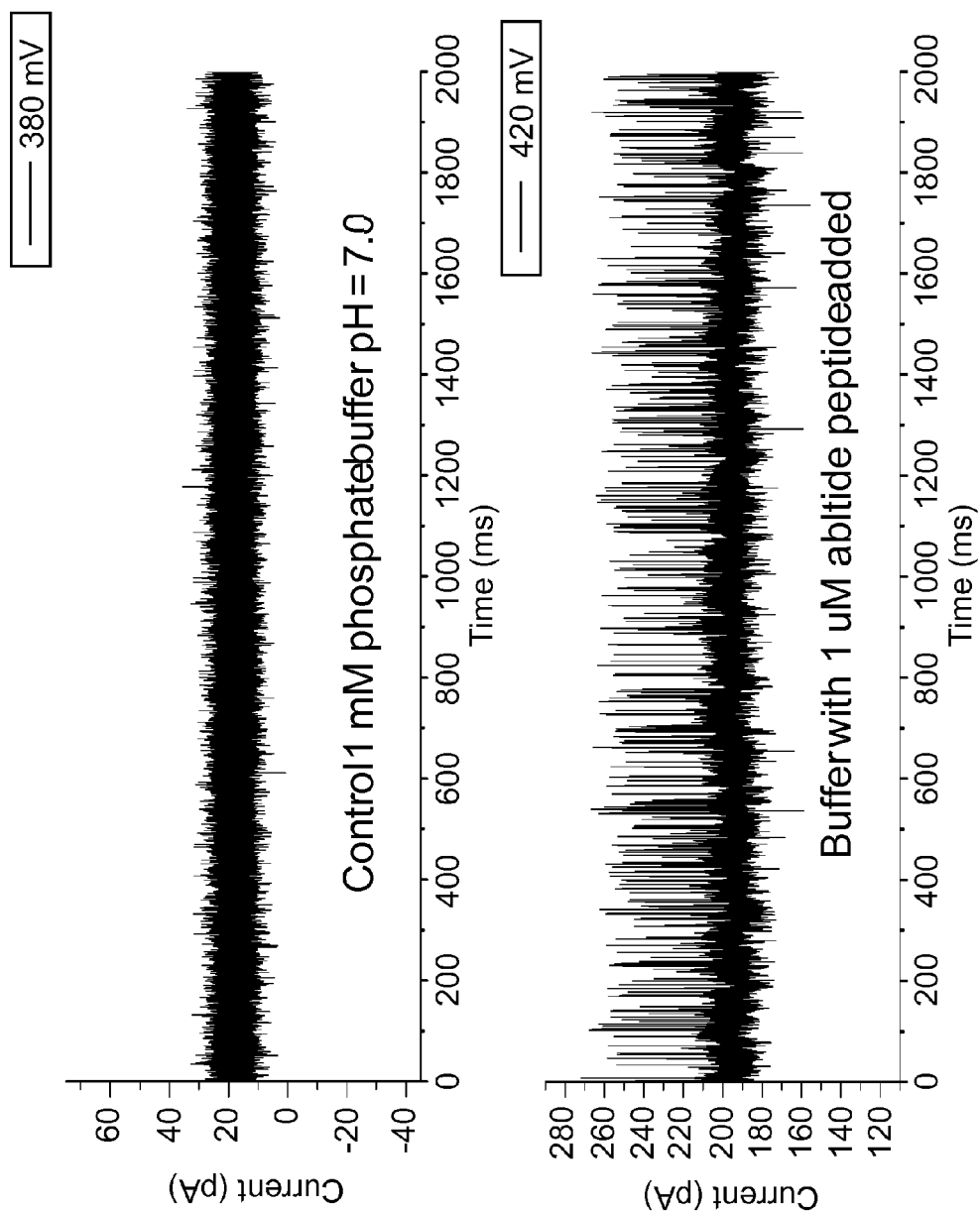
FIG. 16 illustrates a current-signal train generated by 1 µM concentration of the Abltide peptide (with a phosphorylated tyrosine in this case), with respect to some embodiments, where the upper trace shows the control signal in buffer solution alone.
Figure 17:
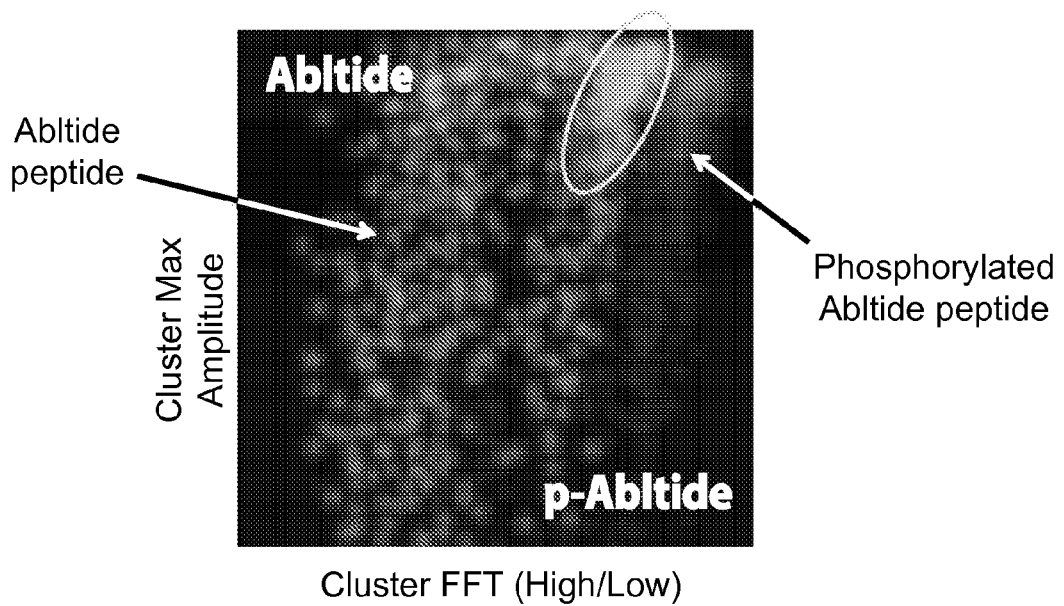
FIG. 17 illustrates signals being different for the phosphorylated and unphosphorylated versions of the Abltide peptide, as shown by a scatter plot of the value of two variables, the cluster amplitude and the ratio of high to low frequency amplitudes of the FFT of the cluster signals.

Using a STM, it has been shown that peptides and amino acids can be identified by means of characteristic features of the recognition tunneling signal (Zhao, Y., B. Ashcroft, P. Zhang, H. Liu, S. Sen, W. Song, J. Im, B. Gyarfas, S. Manna, S. Biswas, C. Borges, and S. Lindsay, *Single Molecule Spectroscopy of Amino Acids and Peptides by Recognition Tunneling. Nature Nanotechnology* 9, 466-473 (2014)). Accordingly, FIG. 16 shows recognition tunneling signals generated by a chip according to some embodiments of the present disclosure, functionalized with ICA molecules. The top trace is a control sample in buffer alone, the bottom trace is a series of signals produced when a 1 μM solution of a peptide (the Abltide sequence, a target for the Abl tyrosine kinase) is added. FIG. 17 shows an example of two characteristics of the signal spike generated by such embodiments, the maximum amplitude in a cluster of signals, and the ratio of the high to low amplitudes in the Fourier transform of a signal cluster, readily separate spikes from the phosphorylated and unphosphorylated peptides. In a 2D probability density map of recorded events, data points from the phosphorylated and unphosphorylated peptides fall into different regions of the plot (there is some overlap in the region marked with an ellipse). Since many drugs target peptides sites for phosphorylation and dephosphorylation, this information may be of clinical significance. As shown above, an analysis like this can be carried out at sample concentrations that may be as low as $10^{-15}$M. In some embodiments, since, the device uses a sample volume of only about 10 ul, amounts of sample as low as $10^{-20}$ Moles (or just 6000 molecules) may be readily detected.

Figure 18:
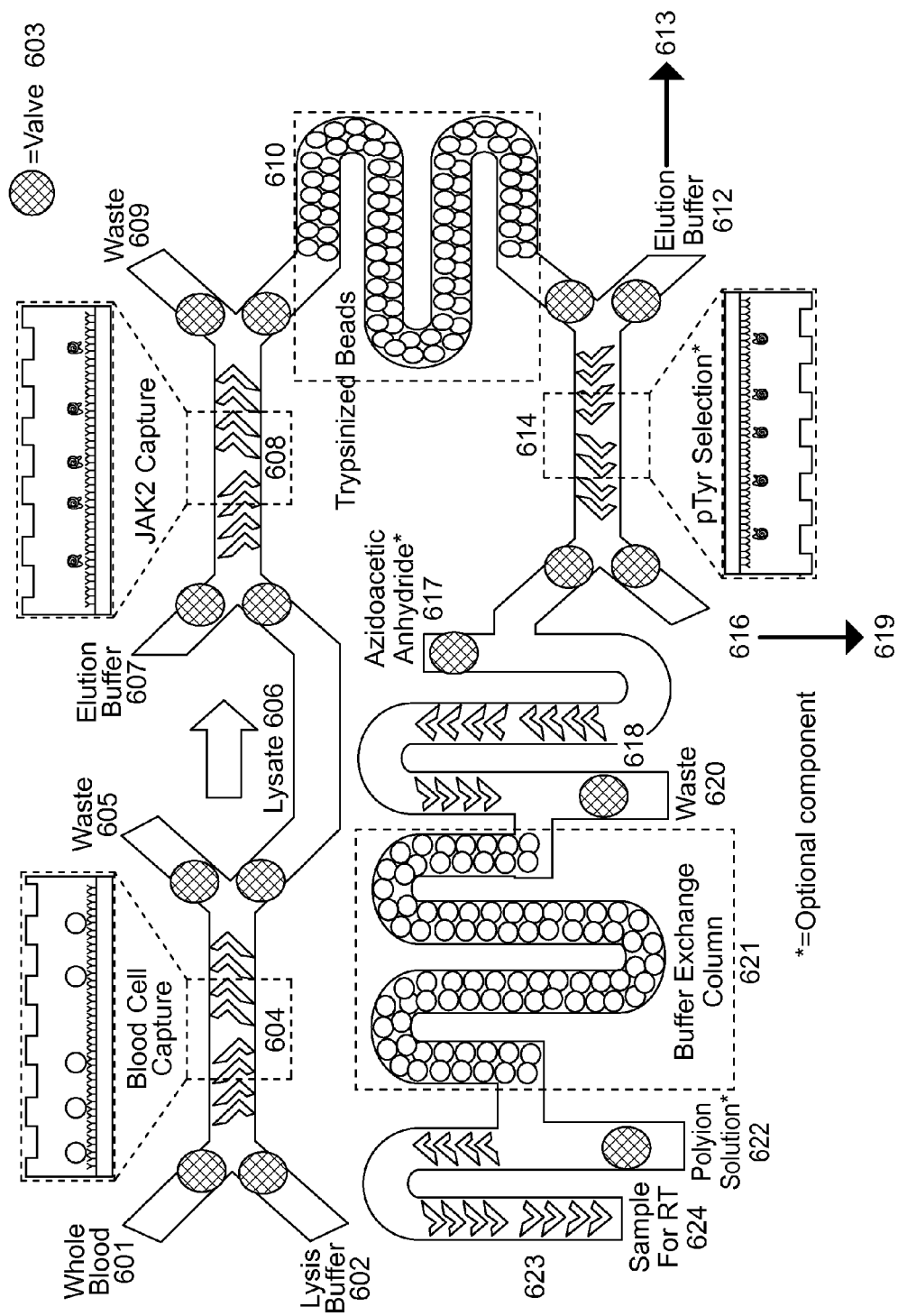
FIG. 18 is a schematic illustration of a lab-on-a-chip configuration for isolating peptides from blood cells, according to some embodiments. Enrichment of phosphorylated tyrosine containing peptides can be added if needed, and reaction with the azidoacetic anhydride and polyion solutions can be added when nanopore based devices are used to further extend the sensitivity.

In clinical applications, such measurements may be limited by the dynamic range of concentrations of analytes present in serum or urine. Therefore, some pre-filtering and selection of targets for analysis may be required. Accordingly, FIG. 18 illustrates a lab-on-a-chip, according to some embodiments, which may be configured to process a clinical sample for presentation a recognition tunneling chip according to some embodiments. In this figure, the design is configured for the example of phosphorylation of the JAK2 kinase using whole blood as the input, but it will be recognized that similar arrangements can be used for many other specific clinical problems. As shown, whole blood is input at 601 to a channel that uses antibodies in a channel 604 to capture blood cells. The captured cells may be lysed with a lysis buffer 602 introduced by means of valves 603 provided the on-chip. Waste may be eluted via 605. The lysate may be eluted via port 606 into, for example, a protein capture channel 608 which may be functionalized with antibodies for the target (shown here as JAK2). Waste may be eluted through port 609. Elution buffer may be used to transfer the isolated proteins via 610 to a channel containing trypsinized beads 611, which generates peptide fragments of the protein which can then be passed out 613 to be sent to the tunnel junction of devices according to some embodiments for analysis.

In some embodiments, in the event that the concentration of modified (i.e. phosphorylated) peptide is too small for detection, the output of the trypsin column 611 can be passed to a further selection channel 614 where antibodies for, e.g., phosphorylated tyrosine, capture the phosphorylated fraction. Waste may be eluted through 616 after which the captured peptides are eluted 619 for transfer to the tunnel junction for counting.

Figure 19:
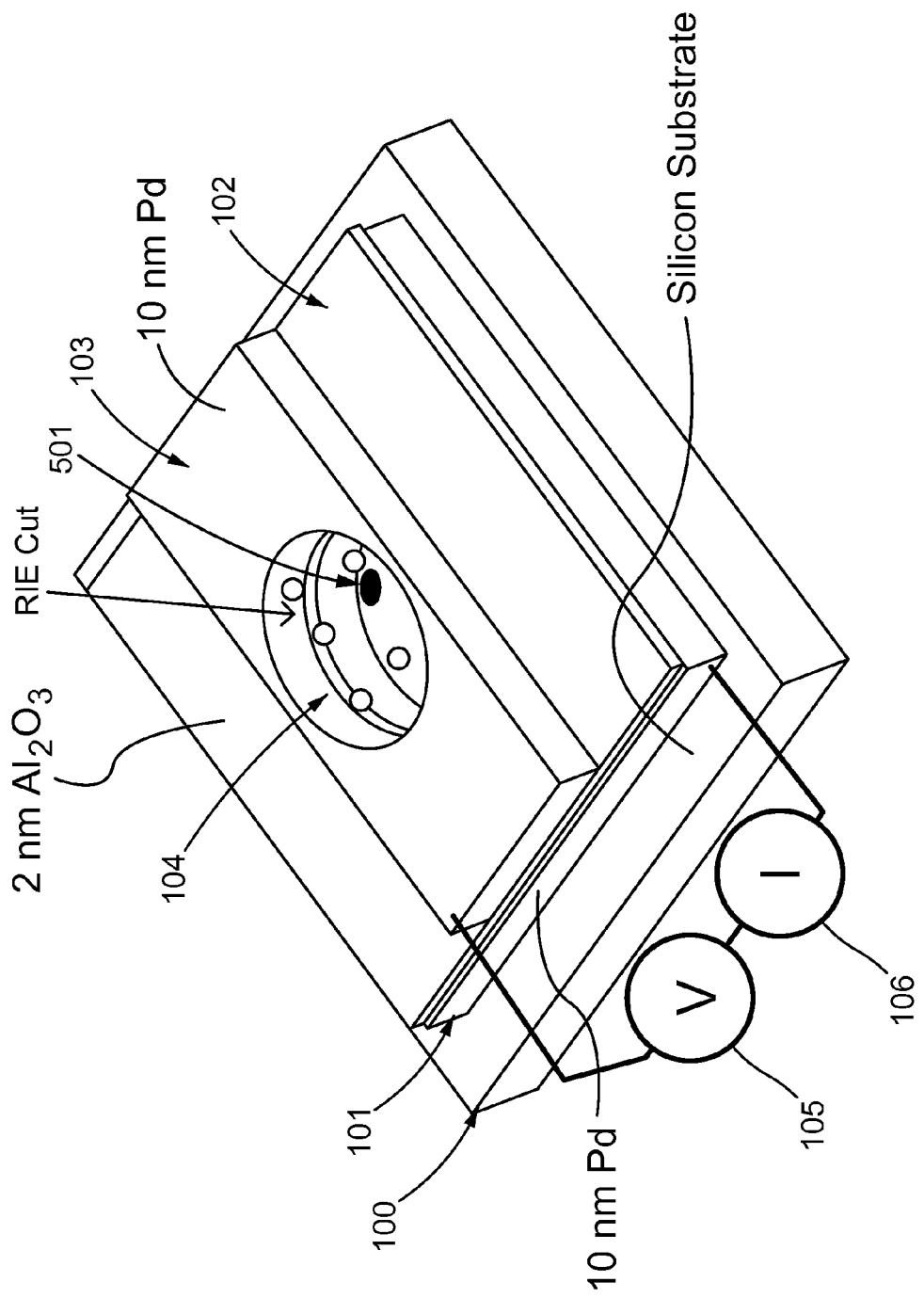
FIG. 19 illustrates a device according to some embodiments for at least one of sequencing a polymer, and for electrophoretic concentration of peptides ligated to charged tails, comprising a device like that shown in FIG. 3, with a further orifice drilled through the lower supporting membrane adjacent to the tunnel junction.

In U.S. provisional patent application No. 61/826,855, entitled, "Improved Chemistry For Translocation Of A Polymer Through A Nanopore" a method is described for concentrating peptides by adding a charged tail to them using azidoacetic anhydride to ligate a charged peptide to the N terminus of the target peptide, and them using electrophoresis to draw the molecules into the tunnel gap. If such further concentration is desired, and additional stage is added to the chip according to some embodiments of the present disclosure. For such a case, peptides may be passed from 614 (or from 613 if enrichment of a modified species is not required or desired) to reaction channel 618 where azidoaceticanhydride 617 is added. The reactants are passed to a buffer exchange column 621 and waste products eluted at 620. The modified peptide can now be reacted with the charged tail (polyion solution) which is added at 622 and the reaction allowed to occur in the channel 623. The eluted complex of peptide and charged tail is collected at 624 to be passed to the tunnel junction of the device according to some embodiments of the present disclosure. One method to implement electrophoretic detection of the target molecule is to incorporate a nanopore into the tunnel junction, as shown in FIG. 19.

Operation of some of the embodiments of the present disclosure can be used with ICA molecules (developed for reading DNA bases), as well as with an argenine-glycine-aspartic acid (RGD) peptide terminated in a cysteine (—SH to bind the metal). In the later, very small concentrations of integrin, the protein that binds the RGD sequence, can be detected. Clearly, any cognate ligand containing a residue or chemical terminus that allows it to be attached to the electrodes can be used in this application.

The device according to some embodiments of the present disclosure may be readily adaptable to strand sequencing of peptides as disclosed in co-pending international application no. PCT/US2013/024130. For such application, the peptide chain is passed by the electrode junction sequentially, such that, a small pore is arranged in close proximity to the electrodes, so that a peptide, pulled through the pore by a charged tail pass each residue by the electrodes. Once the underlying substrate is exposed by RIE (as described above), a small opening 501 can be cut through the remainder of the substrate, as illustrated in FIG. 19. In some embodiments, an opening, placed within a few nm of the electrodes, can be drilled using an electron beam or a helium ion beam without damaging the electrodes (for example).

Figure 20:
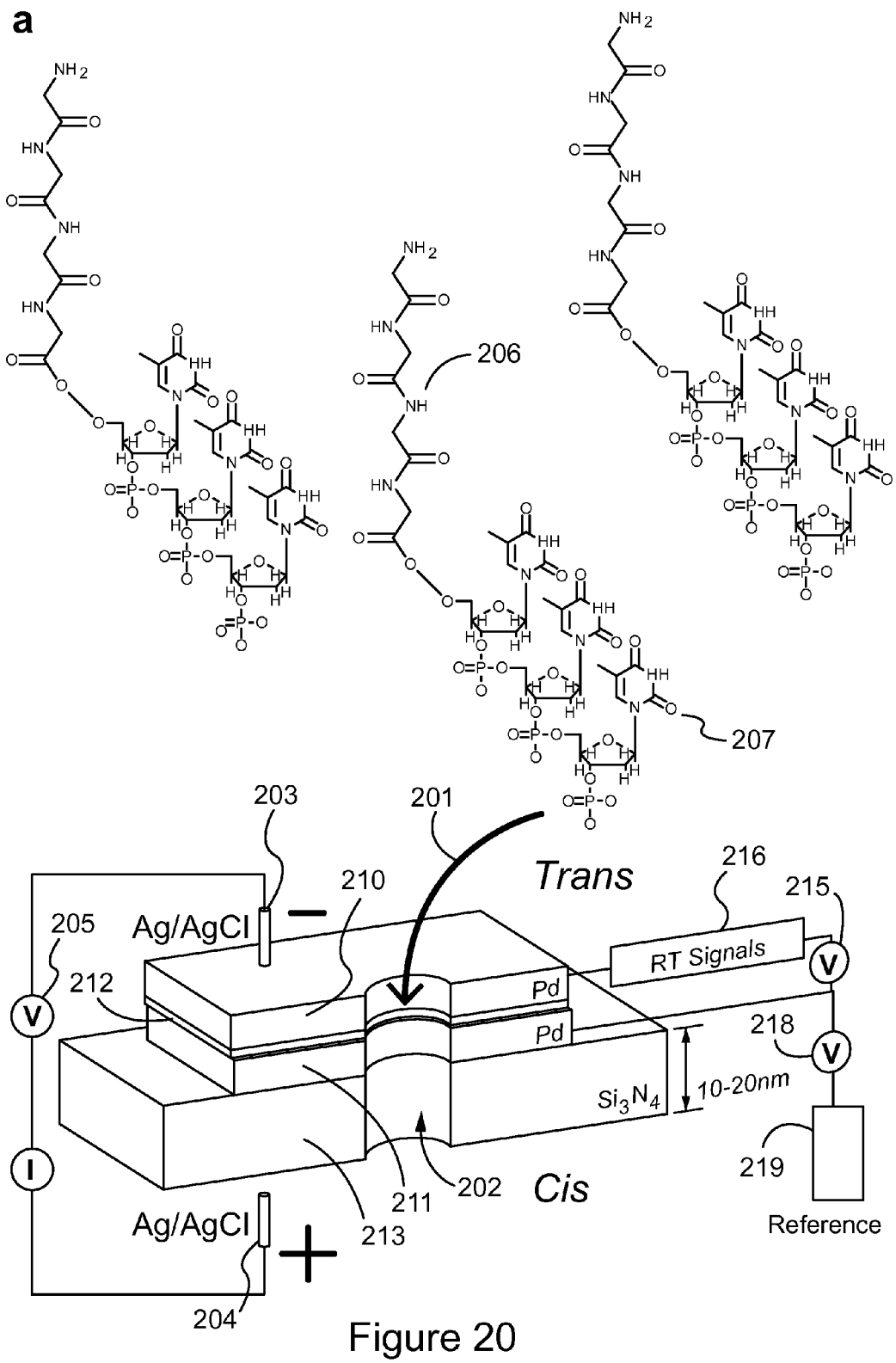
FIG. 20a illustrates an RT junction with a nanopore that allows transit of peptides from one side (Trans) of the chip to the other (Cis), according to some embodiments, where coupling of peptides to charged polymers (shown as d(T)$_3$ here) generates a multitude of counts/second at sub pM concentrations in low salt electrolytes.
FIG. 20b illustrates a microfluidic device for nanopore translocation according to some embodiments, where a recognition tunneling chip (dark slab) is sandwiched between upper and lower chambers.
FIG. 20c illustrates a 10 nm diameter nanopore drilled through an RT device, according to some embodiments, using helium ion FIB.
Figure 20:
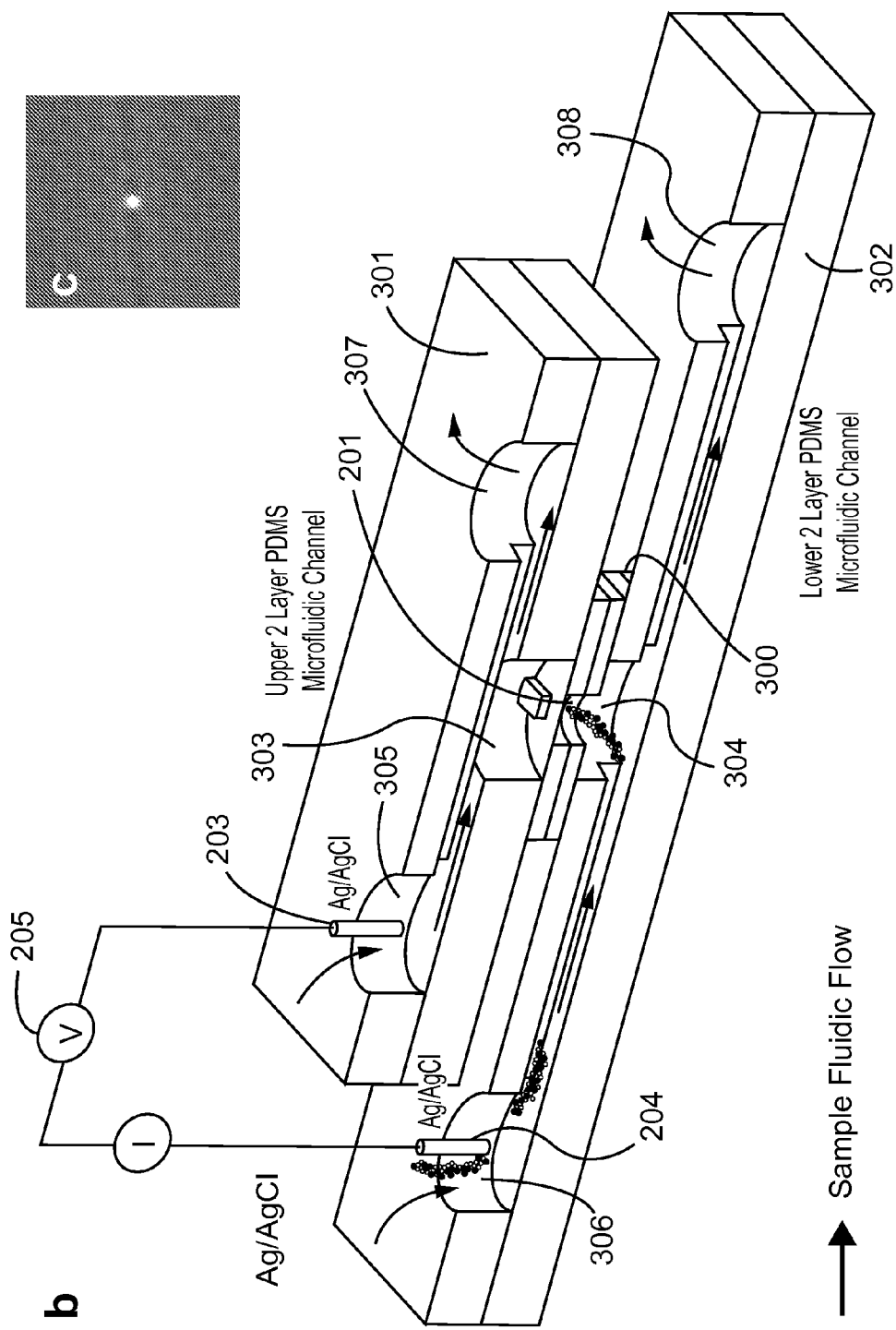

In some embodiments, systems are presented for utilizing a device according to some embodiments, which involves sandwiching the device between two fluid chambers, in fluid communication with each other via a nanopore in the tunnel junction, and providing a biasing components) configured to apply an electric field across the nanopore (for example). One such configuration is shown schematically in FIG. 20a. FIG. 20a shows an overview of a scheme for drawing peptides ligated with a charged tail. A fluid, 201, is in communication with a nanopore 202, an opening connecting the fluid reservoir 201 on the trans side (also referred to as a "trans reservoir") to a second fluid reservoir 202 on the cis side (also referred to as a "cis reservoir"). A first reference electrode 203 is placed in the trans reservoir 201, and second reference electrode 204 is placed in the cis reservoir 202. A bias voltage 205 is applied between the reservoirs 201, 202. When a peptide 206 is tethered to a negatively charged molecule (e.g., such as DNA 207) the reference electrode 204 is made positive with respect to the reference electrode 203 so as to draw the negatively charged molecule 207 into the pore 202 and through the pore, pulling the peptide 206 behind it. This arrangement/approach is reversed for positively charged molecules. The voltage V can be between about 1 mV and about 10V, and can be preferably between about 20 mV and about 500 mV.

The nanopore 202, shown cut open in FIG. 20a, is cut through two palladium electrodes 210, 211 (though other noble metals such as Pt and Au could be used) each of about 1 nm to about 20 nm thickness, and preferably of about 10 nm thickness. The nanopore 202 can be between about 1 nm and about 100 nm in diameter, with about 2 to about 10 nm preferred. The metal layers are separated by a thin dielectric layer 212, made (in some embodiments) from aluminum oxide, though other oxides such as hafnium oxide and/or magnesium oxide can be used. The thickness of this dielectric layer 212 is between about 0.1 to about 100 nm, and preferably about 1 to about 4 nm. The nanopore 202 continues through a dielectric substrate 213 which can be an oxide of silicon, a layer of graphene or $MoS_2$, or, in the preferred embodiment Silicon Nitride. The thickness of this substrate can be about 1 nm to about 100 nm, with about 10 nm to about 20 nm preferred.

A bias 215 is also applied between the two electrodes 210 and 211, and a current to voltage converter device 216 (which may also be referred to as a current monitor) can be used to generate the recognition tunneling signals. The voltage 215 can be between about 1 mV and about 10 V, with about 20 mV to about 800 mV preferred. Either one of the electrodes 210, 211 can be connected to a reference electrode 219 placed into either one of the reservoirs 201, 202. The reference electrode 219 can be biased with a voltage 218 that can be between about 0V and about ±1 V.

An arrangement for creating the two fluid reservoirs 201, 202 is shown in FIG. 20b. The recognition tunneling device 300 (consisting at least of the layers 210, 211, 212 and 213 in FIG. 20a) is sandwiched between two microfluidic devices 301, 302. The microfluidic devices 301, 302 can be made from any elastomer but silicone rubber is preferred. The microfluidic devices 301, 302 contain channels 303, 304 formed so as to direct fluid injected into ports 305 and 306 to contact the upper or lower side of the device 300. Reference electrodes 203 and 204 are embedded in the channels 303, 304. Exit ports 307 and 308 permit fluid to be withdrawn from the channels. In order to achieve a well controlled potential drop across the nanopore 202 formed in the device 300 it is desirable to have the channel be at least about 0.1 mm by about 0.1 mm in cross section and, in some embodiments, no longer than about 10 cm in length.

Any and all references to publications or other documents, including but not limited to, patents, patent applications, articles, webpages, books, etc., presented anywhere in the present application, are herein incorporated by reference in their entirety. However, mention of any reference, article, publication, patent, patent publication, and patent application cited herein is not, and should not be taken as an acknowledgment or any form of suggestion that they constitute valid prior art or form part of the common general knowledge in any country in the world.

Although a few variations have been described in detail above, other modifications are possible. For example, any logic flows depicted in the accompanying figures and/or described herein do not require the particular order shown, or sequential order, to achieve desirable results. Other implementations may be within the scope of at least some of the following exemplary claims.

As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses/devices which may further include any and all elements from any other disclosed methods, systems, and devices, including any and all elements corresponding to binding event determinative systems, devices and methods. In other words, elements from one or another disclosed embodiments may be interchangeable with, or additions to or deletions of, elements from other disclosed embodiments. In addition, one or more features/elements of disclosed embodiments may be removed and still result in patentable subject matter (and thus, resulting in yet more embodiments of the subject disclosure). Also, some embodiments correspond to systems, devices and methods which specifically lack one and/or another element, structure, and/or steps (as applicable), as compared to teachings of the prior art, and therefore represent patentable subject matter and are distinguishable, and thus patentable, therefrom (i.e. claims directed to such embodiments may contain negative limitations to note the lack of one or more features prior art teachings).

What is currently claimed is:

1. A system for determining whether a peptide is phosphorylated or not, the system comprising:
   a first channel configured to receive a sample that includes cells, wherein the first channel includes a first antibody for capturing the cells, and the first channel is further configured to receive a lysis buffer for lysing the captured cells to generate a lysate having a target protein;
   a second channel fluidly coupled to the first channel and configured to receive the lysate, wherein the second channel is functionalized with a second antibody for binding the target protein in the lysate, and the second channel is further configured to receive an eluting solution to generate an elution buffer including the target protein;

a third channel fluidly coupled to the second channel and configured to receive the elution buffer, wherein the third channel is further configured to fragment the target protein to generate a solution including one or more peptides; and a sensing device fluidly coupled to the third channel and configured to receive the one or more peptides, the sensing device comprising (a) a first tunneling electrode, (b) an insulating layer covering a substantial portion of the first tunneling electrode, (c) a second tunneling electrode in contact with the insulating layer, wherein the insulating layer is sandwiched between the first and second tunneling electrodes, and (d) a nanopore through the first and second tunneling electrodes, wherein the nanopore is configured to produce an electrical signal indicative of the phosphorylating status of the one or more peptides when they pass through the nanopore.

2. The system of claim 1, further comprising a fourth channel fluidly coupled to the third channel and configured to receive the solution including the one or more peptides, the fourth channel is functionalized with a third antibody for selectively capturing a subpopulation of the one or more peptides, the fourth channel including an outlet for the subpopulation.

3. The system of claim 2, further comprising a fifth channel fluidly coupled to the third channel or the fourth channel, the fifth channel configured to receive the solution including the one or more peptides or the subpopulation, the fifth channel further configured to modify the one or more peptides or the subpopulation by attaching a charged polymer to each of the one or more peptides.

4. The system of claim 3, wherein the fifth channel includes a buffer exchange column.

5. The system of claim 1, wherein the third channel includes a plurality of trypsinized beads.

6. The system of claim 1, wherein the sensing device further comprises a first reservoir in contact with the first tunneling electrode, and a second reservoir in contact with the second tunneling electrode, wherein the first and second reservoirs are in fluid communication through the nanopore.

7. The system of claim 6, wherein the sensing device further comprises a first reference electrode in the first reservoir.

8. The system of claim 7, wherein the sensing device further comprises a second reference electrode in the second reservoir.

9. The system of claim 1, wherein the nanopore is about 2 nm to 10 nm in diameter.

10. The system of claim 1, wherein the insulating layer is about 1 nm to 4 nm in thickness.

11. The system of claim 1, further comprising a current monitor configured to generate an electrical signal when a molecule passes through the nanopore.

12. The system of claim 1, further comprising a bias voltage source configured to establish a voltage bias between the first tunneling electrode and the second tunneling electrode.

13. The system of claim 1, wherein the protein is JAK2 kinase.

14. The system of claim 1, wherein the sample is whole blood.

15. The system of claim 1, wherein the first and second tunneling electrodes are functionalized by a reader molecule.

* * * * *